United States Patent
Shealy et al.

(10) Patent No.: US 6,233,489 B1
(45) Date of Patent: May 15, 2001

(54) ELECTRICAL STIMULATION TO INCREASE NEUROTENSIN LEVELS

(75) Inventors: C. Norman Shealy, Fair Grove, MO (US); Caroline M. Myss, Melrose Park, IL (US); Leonard Wisneski, Rockville, MD (US)

(73) Assignee: Biogenics II, LLC, Fair Grove, MO (US)

(*) Notice: Subject to any disclaimer, the term of this patent is extended or adjusted under 35 U.S.C. 154(b) by 0 days.

(21) Appl. No.: 09/395,527

(22) Filed: Sep. 14, 1999

(51) Int. Cl.[7] .................................................. A61N 1/36
(52) U.S. Cl. ................................. 607/68; 128/898
(58) Field of Search .............................. 607/2, 68, 69, 607/76; 128/898

(56) References Cited

U.S. PATENT DOCUMENTS

| | | |
|---|---|---|
| 3,929,756 | 12/1975 | Leeman et al. . |
| 5,109,847 | 5/1992 | Liss et al. . |
| 5,374,621 | 12/1994 | Wei . |
| 5,407,916 | 4/1995 | Wise et al. . |
| 5,609,617 | 3/1997 | Shealy et al. .......................... 607/68 |

OTHER PUBLICATIONS

Liss Cranial Stimulator—Professional Instrument Manual, 1994, pp. 1–11.

*Primary Examiner*—Jeffrey R. Jastrzab
(74) *Attorney, Agent, or Firm*—Foley & Lardner (57) ABSTRACT

The endogenous enhancement of neurotensin, an endogenous tridecapeptide, has anti-diabetic, anti-inflammatory, anti-psychotic, neuroleptic and analgesic activity. Exogenous administration of neurotensin causes several side effects. The present invention provides electrical stimulation to increase endogenous neurotensin levels, which provides the benefits of neurotensin without eliciting the unwanted side effects.

12 Claims, 5 Drawing Sheets

CARRIER FREQUENCY
15,000 hz MONOPOLAR

FIG. 3A

1st MODULATOR
15 hz

FIG. 3B

2nd MODULATOR
500 hz

FIG. 3C

TYPICAL COMBINED
WAVEFORM (MONOPOLAR)

FIG. 3D

TYPICAL COMBINED
WAVEFORM (BIPOLAR)

ELECTRICAL STIMULATION TO INCREASE NEUROTENSIN LEVELS

FIELD OF THE INVENTION

This invention pertains to a method for enhancing serum levels of neurotensin in human beings without administration of exogenous neurotensin or salts thereof.

BACKGROUND OF THE INVENTION

Neurotensin, an endogenous tridecapeptide found in the central nervous system, has been postulated to be a neurotransmitter or neuromodulator found in synapsomes in the hypothalamus, amygdala, basal ganglia, and dorsal gray matter of the spinal cord. Neurotensin plays a role in pain perception, but its analgesic effects are not blocked by opioid antagonists. It also affects pituitary hormone release and gastrointestinal function. Though a wide range of pharmacological effects have been attributed to neurotensin, discussion of neurotensin is generally associated with its gastrointestinal activity.

Two important aspects of neurotensin actions on the central nervous system are its possible involvement in the etiology of schizophrenia and its analgesic properties. Nemeroff, et al., Neuropsychopharm 1991; 4:27. Thus, it has been suggested that neurotensin may have neuroleptic-like activity within the central nervous system. Researchers have reported data that showed diminished availability of neurotensin in some psychotic patients with increases in neurotensin early in neuroleptic treatment. These results suggest that neurotensin would be useful as an anti-psychotic agent. Garver, et al., Am. J. Psychiatry 1991; 148:484–8.

Furthermore, it has been reported that neurotensin has analgesic effects when administered intracisternally to rodents. These results suggest that neurotensin would be useful as an analgesic agent. Clineschmidt, et al., European Journal of Pharmacology 1979; 54:129–139.

The C-terminal hexapeptide fragment of neurotensin (NT (8-13)) has been shown to retain much of the activity found in the native peptide. Indeed, neurotensin or NT(8-13) has been shown to possess activity in pre-clinical antinociceptive tests and in animal behavior tests indicative of anti-psychotic efficacy. Irvin, et al., Nature 1981; 29:73-76. NT(8-13) is metabolically unstable and this would diminish its potency as a therapeutic agent. Studies of the catabolism of NT(8-13) in various brain regions have revealed several key amide bonds which are most susceptible to proteolytic degradation. Davis, et al., Journal of Neurochemistry 1992; 58:608–617. Compounds, when administered peripherally, generally do not have sufficient metabolic stability to remain intact long enough to diffuse or to be transported across the blood brain barrier and interact with central neurotensin receptors. As a result, neurotensin has a broad distribution but a very short half-life in blood.

It has been discovered that, when a patient is pretreated with neurotensin, somatostatin inhibits glucagon secretion. At low glucose levels, neurotensin stimulates release of insulin, glucagon, and somatostatin while release of these peptides stimulated by glucose or arginine is inhibited by neurotensin. There is a close similarity between the metabolic effects of neurotensin and those of histamine, and neurotensin effects are reversed by $H_1$ and $H_2$ histamine receptor blockers. Berelowitz, et al., Annals of New York Academy of Science, 1982, Vol. 400, pp. 150–182.

U.S. Pat. No. 3,929,756 to Leeman, et al. discloses the hypothalamically derived substance (and a synthetically prepared tridecapeptide) designated as "neurotensin". The biological activity of neurotensin was described by observing the vassal dilation in rats and was observed to cause a marked increase in vascular permeability following the intravenous injection or interdermal administration.

Forman, et al. studied an interaction of neurotensin with substance P, and suggested that neurotensin is a partial agonist at the substance P receptors on rat mast cells, and in human skin. Br. J. Pharmac. 1982; 77:531–539.

Some other members of the neurotensin family, all of which are strikingly similar in their C-terminal regions, are described by Carraway and Reinecke in their article "Neurotensin and Related Peptides", which appears as Chapter 4 in *The Comparative Physiology of Regulatory Peptides* (Holmgren, editor, Chapmann and Hall, London, 1989). As noted by Carraway and Reinecke, structure and function studies have indicated a strong dependence on the five or six residues of the C-terminal portion of neurotensin and related peptides, and it appears that the C-terminal portion of these peptides is highly conserved in evolution.

In addition, neurotensin, and related peptides, act as anti-inflammatory agonists and, like Corticotrophin-releasing factor, actively shut off the response of tissues to virtually all known inflammatory mediators.

Therefore, there is an existing need to harness the anti-diabetic, anti-inflammatory, anti-psychotic, neuroleptic and analgesic activity of neurotensin despite the extremely short half-life of neurotensin in the body. It would be most beneficial to achieve this objective without the administration of exogenous neurotensin due to the side effects that exogenous sources may cause.

SUMMARY OF THE INVENTION

The present invention provides a method for enhancing or restoring neurotensin in a living human being. Because neurotensin is a naturally occurring neuropeptide, in accordance with the present invention endogenous production of the hormone may be stimulated without requiring the use of exogenous dietary supplements or pharmaceutical preparations containing neurotensin, neurotensin analogs, neurotensin agonists, or salts thereof.

Serum neurotensin levels in human beings may be raised without the use of dietary supplements or pharmaceuticals by applying electrical stimulation to specific epidermal points of the individual's body for a period of time, preferably daily. The electrical stimulation is preferably applied to specific locations on the individual's body which correspond to thirteen well-known acupuncture points. The electrical stimulation can be applied to these acupuncture points over a number of weeks to achieve a significant increase in serum neurotensin levels within the patient. Preferably, electrical stimulation is applied for a minimum period of two to four weeks.

It has been found that the greatest increase in serum neurotensin levels occurred in patients treated with daily electrical stimulation applied to the specific acupuncture points. This electrical stimulation, applied to an individual on a daily basis for a period of several weeks, was effective in elevating neurotensin levels in patient's serum by as much as 500 percent.

Further objects, features and advantages of the invention will be apparent from the following detailed description taken in conjunction with the accompanying drawings.

DETAILED DESCRIPTION OF THE INVENTION

In accordance with the present invention, neurotensin levels may be raised in human beings without the application of exogenous supplements of neurotensin, neurotensin analogs, neurotensin agonists, or their corresponding salts. Stimulating biosynthesis of neurotensin within the body is advantageous over the heretofore known methods of raising serum neurotensin levels, which consisted of neurotensin, neurotensin analogs, neurotensin agonists, or salts thereof, taken either parenterally, intravenously, subcutaneously, or transdermally. Clinical studies of treatments involving administration of neurotensin, its analogs, its agonists, or salts thereof have been associated with undesirable side effects. These side effects include contraction of intestinal and bronchial smooth muscles, increased permeability of venules, and vasopermeability and dilation and stimulation of exocrine glands interrupting negative-feedback control on mediator release. This results in bronchoconstriction, watery extrudation of the conjunctivae, nasal mucosa, and upper respiratory tract airway edema, mucus secretion, and inflammation and ultimately airway obstruction, sneezing and/or coughing.

At low glucose levels, neurotensin stimulates release of insulin, glucagon, and somatostatin, while release of these peptides stimulated by glucose or arginine is inhibited by neurotensin. This can result in constipation and weight gain. These and other side effects from the ingestion of neurotensin, and other undesirable consequences involving an exogenous method of neurotensin administration, can be avoided with the method of the present invention. No side effects have been detected from utilization of the present invention to raise neurotensin levels in patient's blood.

Each of the two apparatus herein described, either alone or in combination with each other, have been found to raise serum neurotensin levels in human beings.

To illustrate performance of the method of the present invention, an apparatus may be used as described in U.S. Pat. No. 5,109,847, the disclosure of which is incorporated by reference. Such apparatus has previously been used to increase serum dehydroepiandrosterone (DHEA) levels in patients by placing electrodes at particular points on an individual's body, specifically, Ring of Fire acupuncture points. See U.S. Pat. No. 5,609,617, the disclosure of which is also incorporated by reference. Such DHEA-enhancing electronic stimulation is preferably performed for five minutes for a period of days at each point on the body where the electrodes are placed.

The method of the present invention is directed to the application of electrical stimulation using the foregoing apparatus to the "Ring of Air" acupuncture points to stimulate the increase of endogenous neurotensin levels. Neurotensin serum levels were found to be significantly increased for a majority of subjects after two weeks of this treatment. In carrying out the invention, a time varying electrical potential stimulus is applied between the first electrode and the second electrode of this device. Such electrical stimulus comprises a low-level voltage (typically yielding a current of less than 4 mA) pulse-train of relatively high frequency, i.e., between 12 and 20 kHz, modulated in amplitude by a relatively low frequency wave in the range of 8 to 20 Hz. The low-frequency wave is preferably non-symmetrical, characterized by a 3:1 duty cycle, being on three-quarters and off one-quarter of the recurring period. By way of example only, the high frequency pulses may occur at a 15 kHz rate at about a 4.0 mA level, while being subject to a 15 Hz modulation with a 3:1 duty factor.

Figure 3A:
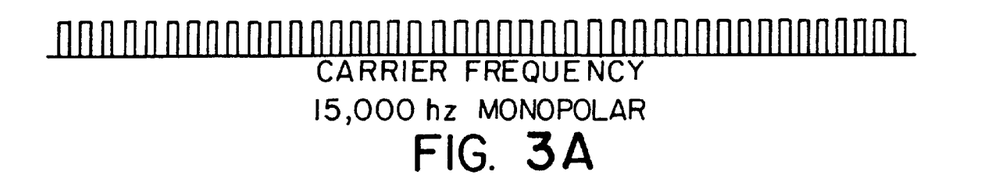
FIG. 3 is a representation of a sample stimulation waveform that may be utilized in the present invention.
Figure 3B:
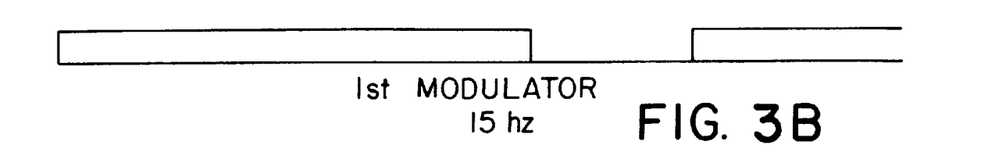
Figure 3C:
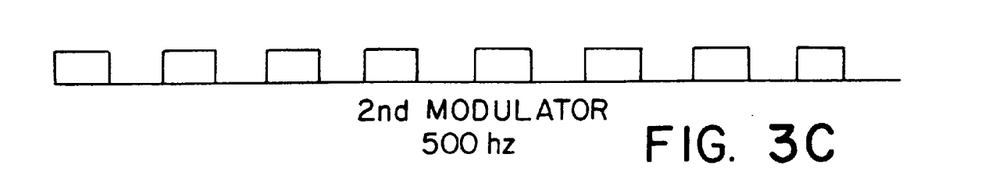
Figure 3D:
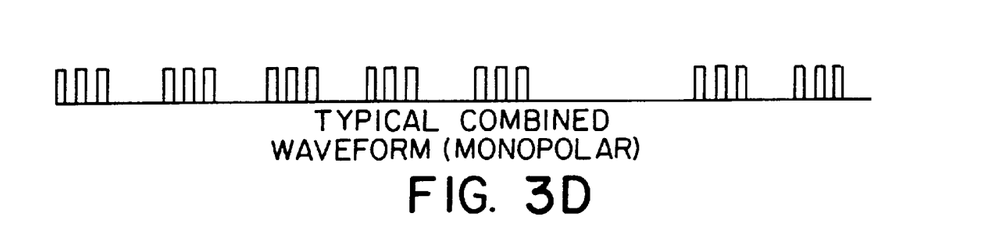

FIGS. 3A through 3E present the various components of a complex waveform of the present invention. More particularly, FIG. 3A is a graphical representation of a carrier frequency signal for one specific time segment. In this example, the carrier frequency is 15 kHz with a duty cycle of 50 percent. FIG. 3B presents the first modulation to the carrier frequency. In this example, the first modulation has a frequency of 15 Hz and a duty cycle of 0.75. The second modulation is depicted in FIG. 3C. The second modulation has a frequency of 500 Hz and a 50 percent duty cycle. The waveform of the carrier frequency signal modulated by the signals of FIGS. 3B and 3C is shown in FIG. 3D (in simplified form) and contains 25 bursts of 15 pulses for each burst. The period for each burst is 2 ms and the period for each pulse is 66.7 $\mu$s. For each, the burst and the pulse, the duty cycle is 50 percent on time.

A cycle for the combined waveform will thus consist of 50 ms "on" time in which the pulses for that frequency combination are generated, and then an "off" time of 16.7 ms.

The complex waveforms of the present invention may be generated with sinusoidal, sawtooth, hyperbolic, or other wave shapes; for clarity, the waveforms presented in FIG. 3, and further discussed below, have been exemplified by a simple square wave.

Figure 3E:
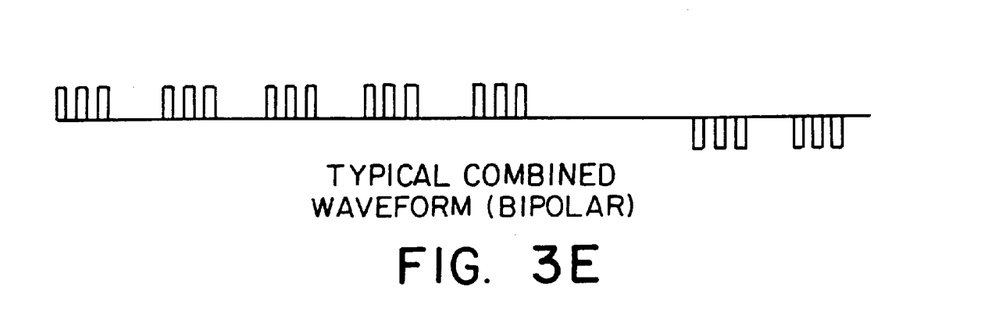

In FIG. 3E, an example of a complex waveform according to the present invention is provided wherein the polarity of the output is switched from positive to negative on a periodic basis, e.g., every 67 ms. This is contrasted with the waveform of FIG. 3D in which the polarity remains positive throughout the cycle; the pulsed DC waveform of FIG. 3D is considered a monopolar output while the output depicted in FIG. 3E is considered bipolar.

For purposes of rough approximation, the energy dissipation in using an electrical stimulator according to the present invention is represented by the area under the pulses depicted in FIG. 3B. It can, therefore, be recognized that adding the second modulation, having a 50 percent duty cycle, results in a 50 percent decrease in power dissipation.

The stimulation circuit may provide any of the following exemplary frequency combinations, (but is not limited to these):

(1) 15 Hz, 500 Hz, 15,000 Hz-monopolar;

(2) 15 Hz, 500 Hz, 15,000 Hz-bipolar (7.5 Hz);

(3) 15 Hz, 500 Hz, 60,000 Hz-monopolar; or (4) 15 Hz, 500 Hz, 60,000 Hz-bipolar.

Figure 4:
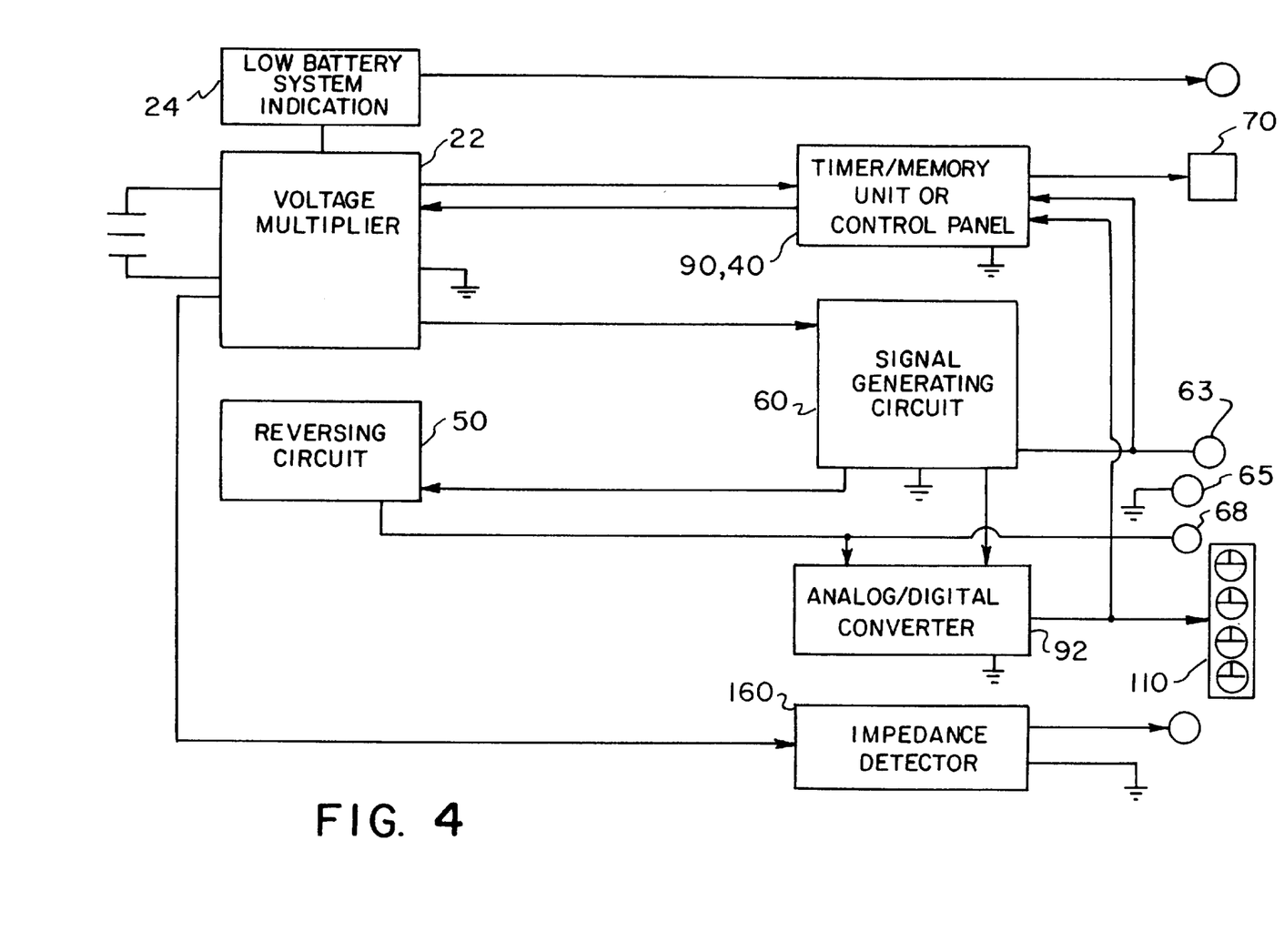
FIG. 4 is a block diagram of an apparatus for generating the stimulation waveform depicted in FIG. 3.

FIG. 4 shows the functional elements of an electrical stimulator used in the present invention. The power source to the electrical stimulator will either be a battery having, e.g., a nominal 9 volt terminal voltage or some rectified and properly transformed line (AC) power source. The battery provides the basic DC power source for generating the complex waveform. This is channeled and controlled by the voltage multiplier 22. The output of a voltage multiplier 22, which is typically between 27–40 volts, is fed to signal generating circuit 60 which is the oscillating circuit that converts the constant DC output into the complex waveform having the desired characteristics.

The specific constant current and current limited waveform generated by signal generating circuit 60 is pre-set by entering the various frequency settings for the two modulations, and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from memory 40.

The signal generating circuit 60 receives the voltage of 27 volts to 40 volts from the voltage multiplier. Within the signal generating circuit 60, the voltage branches off into a carrier frequency and two modulation frequencies. An example of the branching of the waveform is described in FIG. 3.

In FIG. 4, the system supports two separate electrodes for placement on the patient. Electrode 63 represents the positive terminal as generated by signal generating circuit 60. The second electrode 65 is grounded within the circuit. For operation of applying a bipolar waveform, the electrodes are connected to terminals 65 and 68, respectively. Terminal 68 is the output from reversing circuit 50, which may be present and which acts to flip the signal generating circuit pursuant to preset timing constraints.

The following ancillary systems are also present in this circuit. The low battery and system on indicator 24 which monitors the battery output via voltage multiplier 22 generates an alarm signal when battery output voltage drops below the present limit, for example, 7.0 volts. It also shuts the system down if the output voltage falls below the present limit of approximately 6.0 volts.

The analog/digital converter 92 converts the signal from the signal generating circuit 60 so that the patient can read it. The analog/digital converter 92 reads the level of output and converts it to the appropriate signal for the four-gate integrated circuit which uses that signal to turn on the appropriate sequence of 4 LEDs 110.

Finally, the impedance detector 160 is used to determine if the system is being used on a person (as opposed to someone just running the system without attaching it to a person).

Figure 5:
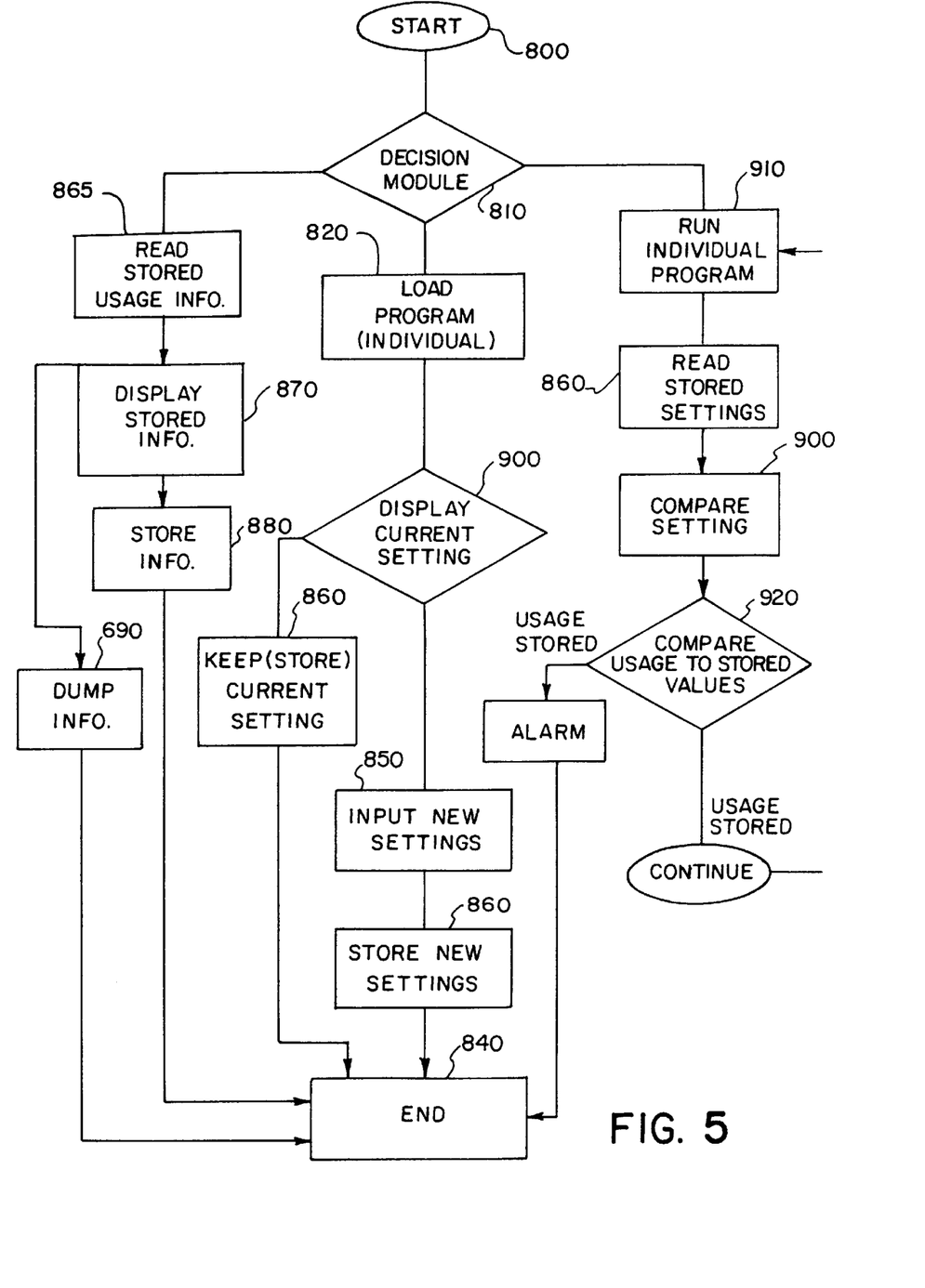
FIG. 5 is a logic flowchart of a data processing program controlling the operation of the apparatus of FIG. 4.

FIG. 5 is a flowchart of the timer unit 90 which the apparatus will use to monitor usage by the patient. This program will prevent the patient from misusing the electrical stimulator apparatus and will allow the physician to set an individual treatment program and to monitor the patient's compliance to the set program. The timer unit 90 will allow the therapist to set the number of days the system is to be used, the number of times per day the system will be used, and the time duration for each use.

The program 800 starts with an Origination Decision Module 810. The Original Decision Module 810 will give the therapist three choices for use. If the Individualized Program 820 pathway is chosen, the timer unit will load the Individualized Program 820. Then the Individualized Program 820 will begin with a display showing the Current Setting 900, for each of the parameters (i.e., the number of days of use, the number of times per day of use, and the length of time for each use). Next, the program will ask the therapist whether he or she wants to keep the current settings 855 or Input New Settings 850. If the therapists wishes to use the same settings as already registered in the program 800, the Individualized Program 820 will Store 860 the values and will End 840. However, if the therapist wishes to change the settings, the program will proceed to the Change Input Values 850 module in which the computer will ask the therapist for the new values for the settings. Then the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870, and the therapist will decide whether to store the patient information in the Patient Storage Module 880, or else it will Dump the information 890 and it will End 840. A final selection which the therapist may access through the Origination Decision Module 810 is actually to use the system. If this choice is inputted, the Run Timed Program 910 will be initialized. The Run Timed Program 910 will read the Stored 860 values. Then the program will Check 920 and Stored 860 values against the current running settings 900 which are the values of the Run Timed Program 910 for this usage of the system. If the current running settings 900 for the number of days of use is greater than the Stored 860 values, the program will End 840 without the system being turned on. Next, the Run Timed Program 910 will check the value of the Stored 860 values for the number of uses for a given date and, if the current running settings 900 is greater than the Stored 860 values for the number of uses for a day, the system will End 840 for that day and the system will not be able to be used until the next day. Finally, as the system is being used, a Running Time Clock will be compared to the Run Timed Program 910, and when the current running settings in 900 are greater than the Stored 860 values for the length of time for that session, the system will End 840 for that session and the system will not be able to be used until the next session period.

The LISS Cranial Stimulator (MEDIC Consultants, Inc., 265 Vreeland Avenue, Patterson, N.J.) is a commercially available device which provides an electrical signal equivalent to the corresponding signal described above. The LISS Cranial Stimulator has been previously shown to reduce symptoms of depression, anxiety, and insomnia, when the electric signal from the LISS Cranial Stimulator was applied bitemporally to individuals showing signs of these problems. The device is the preferred electrical stimulator which produces a high frequency electrical wave bearing a low frequency amplitude modulation to a pair of electrodes used in the present invention.

The LISS Cranial Stimulator was ineffective, however, in raising neurotensin serum levels in patients when the device was used bitemporally. It is only through the use of the LISS Cranial Stimulator in the heretofore unknown method of applying electrical stimulation in a set of acupuncture points known as the Ring of Air whereby serum neurotensin levels were found to be significantly increased in many individuals.

Another form of electric stimulation of individuals has been found to increase serum neurotensin levels in individuals. This stimulation may be applied by use of an apparatus capable of delivering a very high frequency electrical stimulus, e.g., up to 300 GHz at an energy level of up to 1 $\mu$V. This apparatus, referred to as a GigaTENS™ Electrical Stimulator, is used to provide the proper electrical stimulation to the individual to raise neurotensin serum levels by placing the electrode from the device on specific points of an individual's body, and applying a very high frequency electrical stimulus, e.g., up to 30 GHz at a power level of $10^{-9}$ W/cm$^2$, and preferably at 52 to 78 GHz at an electrical power of $10^{-9}$ W/cm$^2$, in a sequential manner to each of the specific points, corresponding to the Ring of Air, on the individual's body for a period of about three minutes per day on a daily basis for a period of about at least two weeks.

Figure 1:
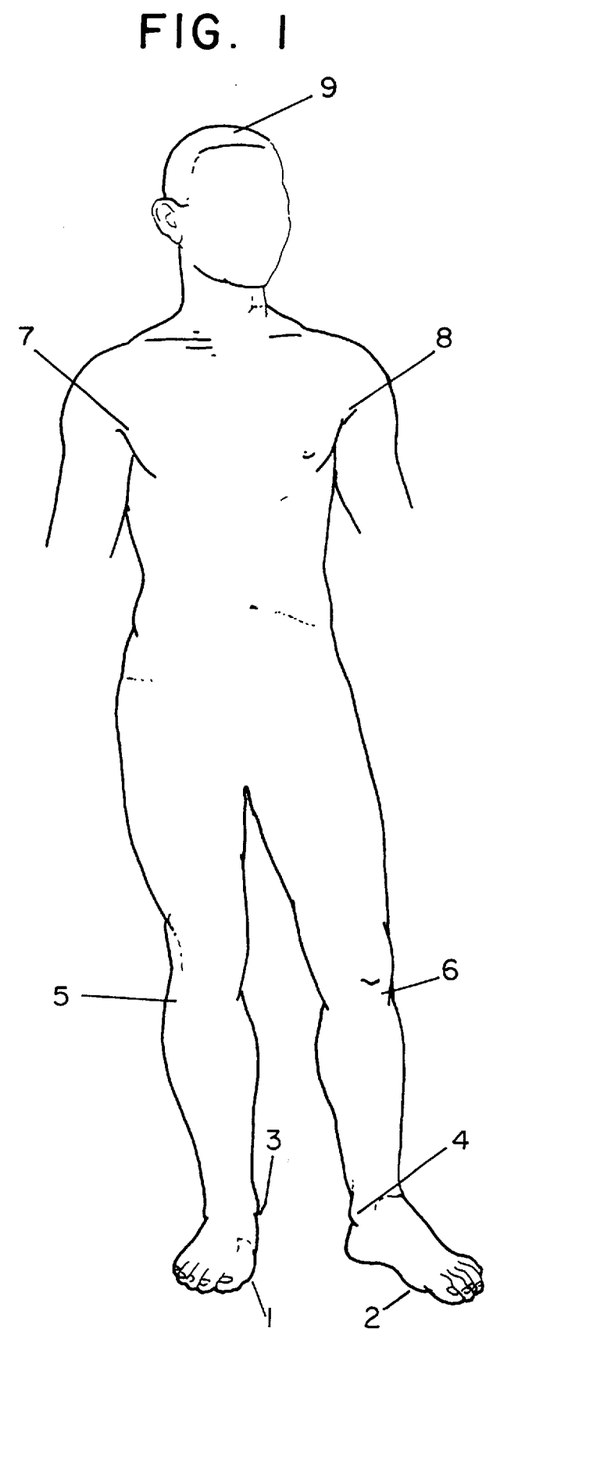
FIG. 1 is a frontal sketch of a human being illustrating nine acupuncture points included in the Ring of Air.
Figure 2:
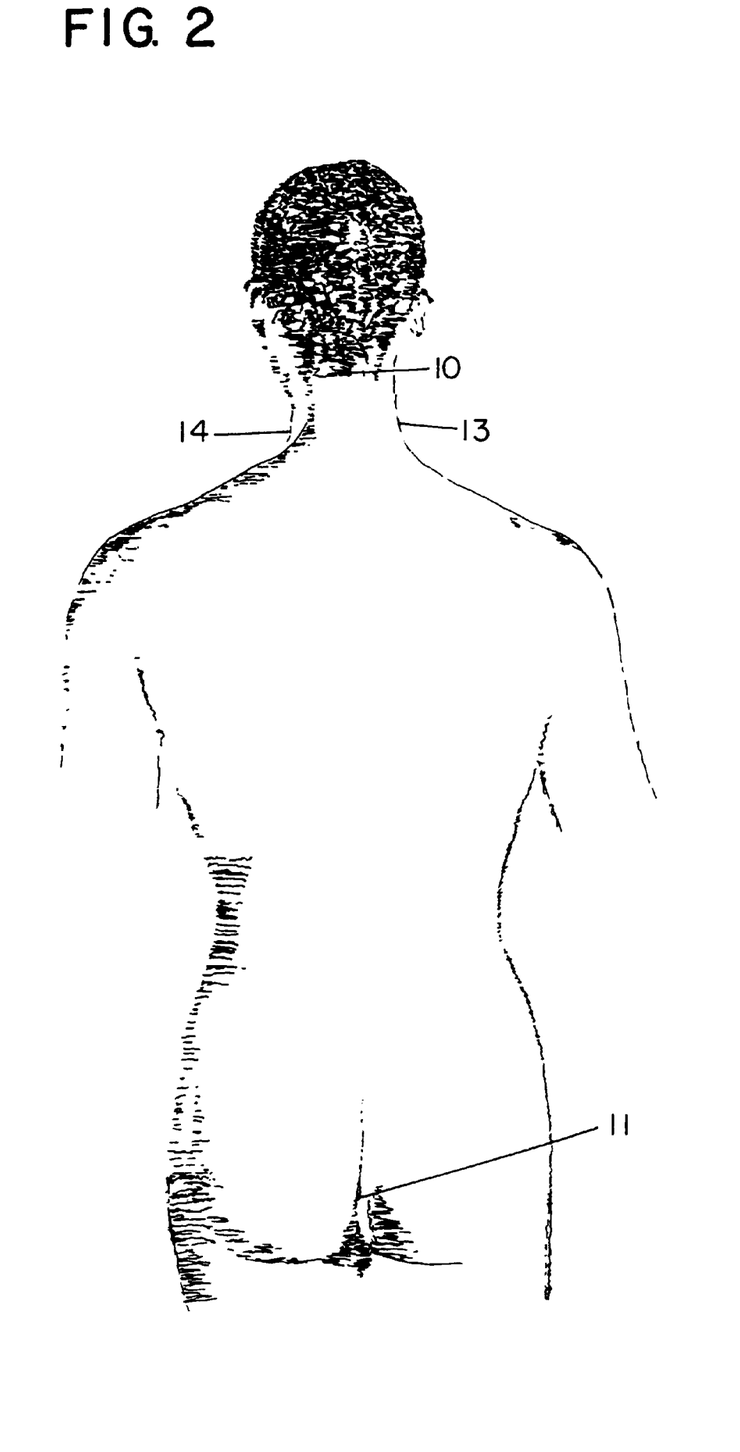
FIG. 2 is a back profile sketch of a human being illustrating four acupuncture points included in the Ring of Air.

These specific points on the individual's body correspond to thirteen specific acupuncture points, hereinafter defined as the "Ring of Air." These thirteen points correspond to well-known acupuncture points located in various places on the body. The position of these various points are roughly illustrated on FIGS. 1 and 2, and correspond to the acupuncture points of SP1a, LIV3, S36, L1, G20, G31, 16, 20. Positions 1 and 2 are the medial side of great toe-corner of nail; positions 3 and 4 are finger length back from front of great toe and to inside foot; positions 5 and 6 are outside of knee cap down to "bony knot" and below; positions 7 and 8 are located by finding shoulder joint—then move down to soft tissue above arm pit; positions 12 and 13 are 1 inch on either side of spine at occipital area (soft area below base of skull); positions 10 and 11 are bottom of skull (flex head to find soft tissue movement) and bottom of tailbone; and position 9 is center top of head. Although these acupuncture points are well known in Chinese acupuncture literature, it has been surprisingly and unexpectedly discovered in accordance with the invention that this combination of acupuncture points, i.e., the Ring of Air, can be electrically stimulated to raise neurotensin serum levels in individuals.

The invention is further illustrated by the following example, which is not to be construed as limiting, but merely as an illustration of some preferred features of the invention.

EXAMPLE

The neurotensin levels of individuals participating in the study were initially determined prior to neurotensin enhancement by the present invention. All neurotensin serum measurements of samples of blood taken from the subjects were performed by Pennsylvania State Geisinger Laboratories, Hershey, Pennsylvania. These neurotensin serum measurements are accurate to within +/−4 percent. From these measurements, it appears that the optimal neurotensin serum levels for men is in the range of 16+/−4 pmol/l, with a mean value for the men tested of 12 pmol/l. It was noted that exceptionally healthy persons had serum neurotensin levels at the upper end of the range determined, independent of the age of the individual tested. Overall, the healthiest individuals in this sample had neurotensin levels 20 percent or more above the mean. In addition, patients treated at the Shealy Institute (1328 E. Evergreen, Springfield, Mo.) for a period of three years who evidenced any type of illness generally had neurotensin serum levels well below the appropriate mean neurotensin serum levels for their sex.

In one set of trials with ten individuals, the GigaTENS™ Electrical Stimulator was applied for three minutes daily to each acupuncture point in the Ring of Air for up to twelve weeks. In seven subjects in the study, neurotensin levels increased by 50 to 500 percent. In three of the ten subjects, no increase or a decrease was observed. The results of this study are shown in Table 1. Three individuals who had shown enhancements in their neurotensin serum levels stopped using the GigaTENS™ after four weeks, and their neurotensin levels declined again over the next month to their initial value.

TABLE 1

ENHANCEMENT OF SERUM NEUROTENSIN (NT) LEVELS VIA APPLICATION OF GigaTENS ™ TO THE RING OF AIR

| SUBJECT | GENDER | NT BEFORE | NT AFTER |
| --- | --- | --- | --- |
| 1 | M | 7.9 | 8.9 |
| 2 | M | 9.3 | 7.7 |
| 3 | M | 3.0 | 3.0 |
| 4 | M | 9.0 | 11.2 |
| 5 | M | 8.4 | 14.9 |
| 6 | M | 8.5 | 43.3 |
| 7 | M | 3.0 | 3.0 |
| 8 | M | 3.0 | 35.5 |
| 9 | M | 13.1 | 37.7 |
| 10 | M | 3.0 | 13.1 |

To obtain the best results in stimulating natural production of neurotensin in patients, it is preferred to utilize electrical stimulation of the Ring of Air acupuncture points using a combination of the GigaTENS™ Stimulator and the LISS Cranial Stimulator. Preferably the GigaTENS™ Stimulator is used on the Ring of air acupuncture points daily for a period of 5 consecutive days and the LISS Cranial Stimulator is used on the Ring of Air acupuncture points for the following two consecutive days. For example, in a preferred treatment, the 13 Ring of Air acupuncture points are stimulated daily from Monday through Friday with the GinaTENS™ Stimulator and then the same points are stimulated with the LISS Crainial Stimulator daily on Saturday and Sunday. Preferably, stimulation of the 13 Ring of Air acupuncture points is conducted for 30 minutes with the LISS Cranial Stimulator and for three minutes with the GigaTENS™ Stimulator. Stimulation of the 13 Ring of Air acupuncture points using the LISS Cranial Stimulator and GigaTENS™ Stimulator may be matched to the individual treatment needs and may occur over a more prolonged period than the 7-day treatment discussed above. In a more preferred method of increasing serum neurotensin values the above procedure is repeated so that the treatment is conducted for at least two weeks. For example, in certain preferred treatments, electrical stimulation is applied to the Ring of Air acupuncture points for approximately five minutes once per day for at least 14 days.

As discussed supra, neurotensin has anti-diabetic, anti-inflammatory, anti-psychotic, neuroleptic and analgesic activity. Thus, the enhancement of endogenous neurotensin levels provides the benefits of neurotensin without eliciting the unwanted side effects concomitant with the administration of exogenous sources of neurotensin.

The present invention may be embodied in other specific forms without departing from its spirit or its central characteristics. The described embodiments are to be considered in all respects only as illustrative and not restrictive. The scope of the invention is, therefore, indicated by the following claims, rather than by the foregoing description. All changes which come within the meaning and range of equivalency of the claims are to be embraced within their scope.

What is claimed is:

1. A method of raising serum neurotensin levels in an individual comprising the steps of:

(a) applying electrodes sequentially to at least one acupuncture point selected from a Ring of Air acupuncture point of the individual's body; and (b) applying a high frequency of at least one kHz electrical stimulus bearing a low-frequency amplitude modulation to the electrodes at each selected acupuncture point repetitively over a period of time sufficient to result in stimulation of endogenous production of neurotensin within the individual.

2. The method of claim 1 wherein the electrical stimulation is applied for a period of time of approximately five minutes of each acupuncture point at least once per day for a period of at least 14 days.

3. The method of claim 1 wherein the frequency of the high-frequency electrical stimulation is in the range of 12 to 20 kHz, modulated by low-frequency amplitude modulation in the range of 8 to 20 Hz, and wherein the current applied to the individual by the electrical stimulation does not exceed about 4.0 mA.

4. The method of claim 3 wherein the amplitude of the modulation is non-symmetrical.

5. The method of claim 1 wherein the electrical stimulus is a frequency of 52 to 78 GHz and further comprises a power level of $10^{-9}$ W/cm$^2$.

6. A method of raising serum neurotensin levels in an individual comprising the steps of:
   (a) applying a first electrode sequentially to at least one acupuncture point selected from a Ring of Air acupuncture points of an individual's body;
   (b) applying a high frequency electrical stimulus bearing a low-frequency amplitude modulation to the first electrode at each acupuncture point;
   (c) applying a second electrode sequentially to at least one Ring of Air acupuncture point of the individual's body;
   (d) applying a high-frequency electrical stimulus to the second electrode at each acupuncture point;
   (e) repeating steps (a) through (d) repetitively over a period of time sufficient to result in stimulation of endogenous production of neurotensin within the individual.

7. The method of claim 6, wherein steps (a) through (d) are repeated on each of the thirteen Ring of Air acupuncture points of the individual's body, and the high frequency electrical stimulas is conducted for at least 3 minutes at each Ring of Air acupuncture point.

8. The method of claim 7 wherein, steps (a) through (d) are repeated daily over a period of at least one week; wherein the high frequency electrical stimulus is conducted for a period of at least 3 minutes for the first five consecutive days of the week using an electrical stimulator delivering up to 78 GHz at an electrical power up to about $10^{-9}$ W/cm$^2$; and further wherein the high frequency electrical stimulus is conducted for a period of at least 3 minutes for the last two consecutive days of the week using an electrical stimulator delivering a current of up to 4 mA in a pulse train having a frequency of from about 12 to about 20 kHz modulated in amplitude by a frequency wave ranging from about 8 to about 20 Hz.

9. A method of raising serum neurotensin levels in an individual comprising the steps of:
   (a) applying electrodes, the electrodes attached to an electrical generator, to sets of acupuncture points sequentially at each of the acupuncture points; and
   (b) applying a moderately high frequency from the electrical generator to the electrodes of at least one kHz having an electrical amplitude which does not exceed 2 mA, to stimulate endogenous production of neurotensin within the individual.

10. The method of claim 9 wherein the step of applying the electrical stimulus further comprises applying the electrical stimulus for a period of at least five minutes to the electrodes.

11. A method of raising serum neurotensin levels in an individual comprising the steps of:
   (a) applying electrodes sequentially to at least one acupuncture point selected from a Ring of Air acupuncture point on an individual's body;
   (b) applying an electrical stimulus having a frequency of 52 to 300 GHz sequentially to the electrodes at each of the selected Ring of Air acupuncture points; and
   (c) continuing electrical stimulus for approximately three minutes at each point to stimulate endogenous production of neurotensin within the individual.

12. The method of claim 11 wherein the amplitude of the current does not exceed 1 microvolt on any one acupuncture point.

* * * * *